US00PP23906P3

(12) United States Plant Patent
Kardos

(10) Patent No.: US PP23,906 P3
(45) Date of Patent: Sep. 17, 2013

(54) *LAGERSTROEMIA* PLANT NAMED 'PURPLE MAGIC'

(50) Latin Name: ***Lagerstroemia* hybrid**
Varietal Denomination: Purple Magic

(75) Inventor: Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 91 days.

(21) Appl. No.: 13/373,362

(22) Filed: Nov. 10, 2011

(65) Prior Publication Data

US 2013/0125275 P1 May 16, 2013

(51) Int. Cl.
*A01H 5/00* (2006.01)

(52) U.S. Cl.
USPC ..... Plt./252

(58) Field of Classification Search
USPC ..... Plt./252
See application file for complete search history.

(56) References Cited

U.S. PATENT DOCUMENTS

| | | | |
|---|---|---|---|
| PP16,917 | P2 | 8/2006 | Dirr |
| PP17,411 | P2 | 2/2007 | Dirr |
| PP22,161 | P2 | 9/2011 | Dirr |
| PP23,071 | P3 | 9/2012 | Dirr |
| PP23,168 | P3 | 11/2012 | Griffith |
| PP23,178 | P3 | 11/2012 | Dirr |
| 2013/0007933 | P1 | 1/2013 | Kardos |

OTHER PUBLICATIONS

Plant Introductions, Inc. webpage, (downloaded Nov. 3, 2011) "*Lagerstroemia*" selections, http://www.plantintroductions.com/lagerstroemiaselections.html, Plant Introductions, Inc., 6 pages.

*Lagerstroemia* 'Purple Magic' Catalog Page (distributed at a trade show Jan. 5, 2011) Plant Introductions, Inc., 1 page.

*Primary Examiner* — Kent L Bell
(74) *Attorney, Agent, or Firm* — Lathrop & Gage LLP

(57) ABSTRACT

A new and distinct cultivar of *Lagerstroemia* plant named 'Purple Magic', characterized by its compact, rounded to upright intermediate growth habit, reddish new growth, lustrous dark green foliage in summer, purple flowers, and resistance to powdery mildew and *Cercospora* leaf spot.

3 Drawing Sheets

Genus and species of plant claimed: *Lagerstroemia* hybrid. Variety denomination: 'Purple Magic'.

BACKGROUND OF THE INVENTION

The present invention relates to a new and distinct cultivar of *Lagerstroemia* plant, botanically known as *Lagerstroemia* L., commonly known as crapemyrtle, and hereinafter referred to by the cultivar name 'Purple Magic'. 'Purple Magic' is grown primarily as an ornamental for landscape use and for use as a potted plant.

'Purple Magic' originated from open-pollinated seed of an unnamed and unpatented seedling known to the inventor as 16-02 growing in Watkinsville, Ga. The cultivar 'Purple Magic' originated and was selected in a cultivated environment in Watkinsville, Ga. from the progeny of this open-pollination by continued evaluation for growth habit and foliage and flower characteristics.

Asexual reproduction of 'Purple Magic' by stem cuttings in Watkinsville, Ga. since 2008 has shown that all the unique features of this new *Lagerstroemia,* as herein described, are stable and reproduced true-to-type through successive generations of such asexual propagation.

SUMMARY OF THE INVENTION

Plants of the new cultivar 'Purple Magic' have not been observed under all possible environmental conditions. The phenotype may vary somewhat with changes in light, temperature, soil and rainfall without, however, any variance in genotype.

The following traits have been repeatedly observed and are determined to be unique characteristics of 'Purple Magic'. These characteristics in combination distinguish 'Purple Magic' as a new and distinct cultivar: 1. Compact, rounded to upright intermediate growth habit; 2. Reddish new growth; 3. Lustrous dark green foliage in summer; 4. Purple flowers; 5. Resistance to powdery mildew and *Cercospora* leaf spot.

Plants of 'Purple Magic' differ from plants of the parent, 16-02 (unpatented), primarily in growth habit, flower color, and disease resistance. Plants of 16-02 have a large upright spreading growth habit, pale lavender-purple flowers, and are moderately susceptible to powdery mildew and *Cercospora* leaf spot, whereas plants of 'Purple Magic' have a more compact, rounded to upright intermediate growth habit, purple flowers, and are resistant to powdery mildew and *Cercospora* leaf spot. 'Purple Magic' can be compared to the cultivar 'Catawba' (not patented), but differs in size, growth habit, and flower color. 'Purple Magic' has a smaller, rounded to upright growth habit and darker purple flowers, whereas 'Catawba' has a larger globose growth habit and lighter purple flowers. 'Purple Magic' can be compared to the cultivar 'GAMAD IX' (U.S. Plant Pat. No. 23,560), but differs in size, growth habit, and flower color. 'Purple Magic' has a larger, rounded to upright growth habit and darker purple flowers, whereas 'GAMAD IX' has a smaller, rounded to broad-rounded growth habit and lighter purple flowers.

BRIEF DESCRIPTION OF THE DRAWINGS

The accompanying color photographs illustrate the flower and foliage characteristics and the overall appearance of 'Purple Magic', showing the colors as true as it is reasonably possible to obtain in color reproductions of this type. Colors in the photographs may differ slightly from the color values cited in the detailed botanical description which accurately describe the colors of the new *Lagerstroemia*.

DETAILED DESCRIPTION

Figure 1:
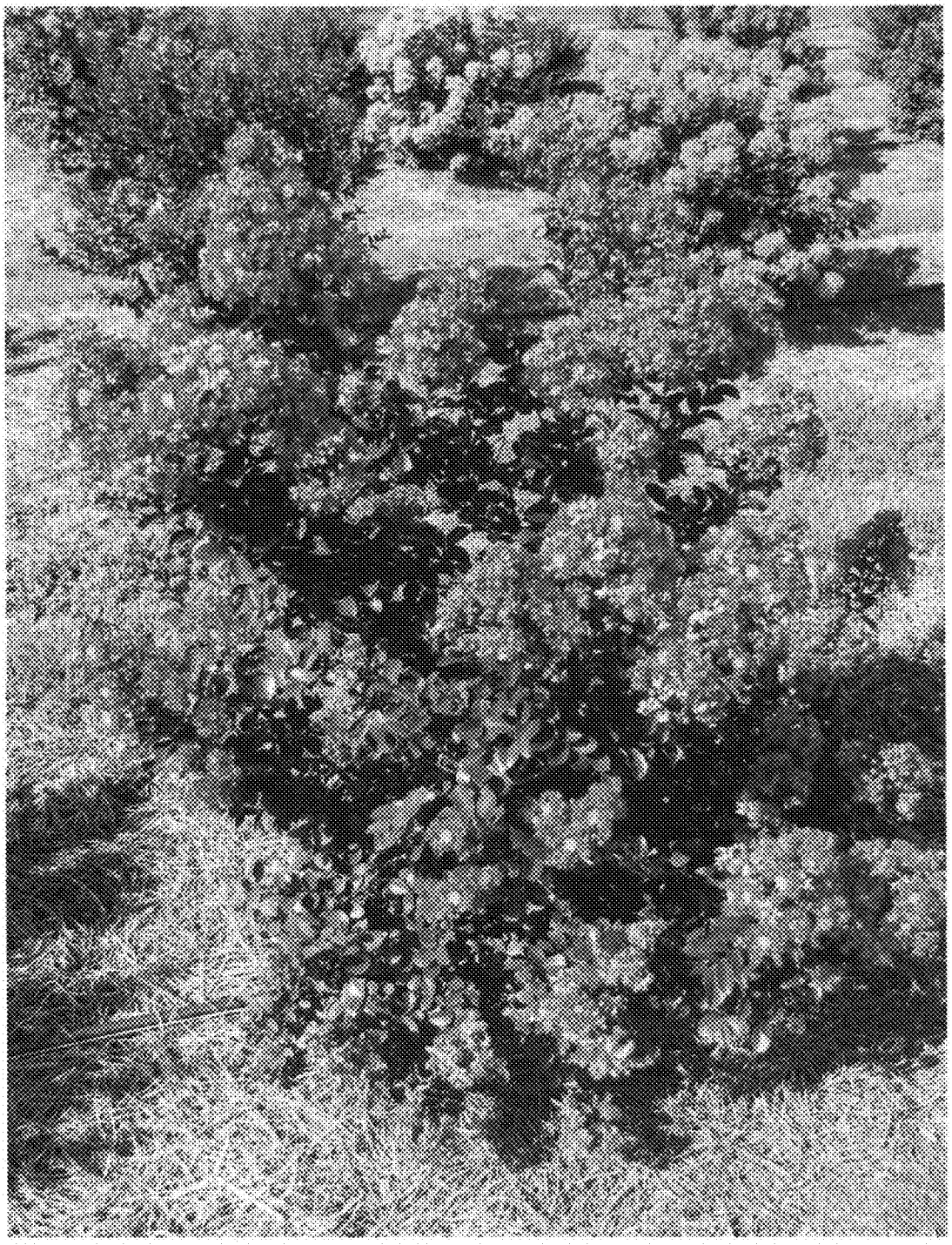
FIG. 1 illustrates the overall appearance of an established plant of 'Purple Magic' planted in the ground.
Figure 2:
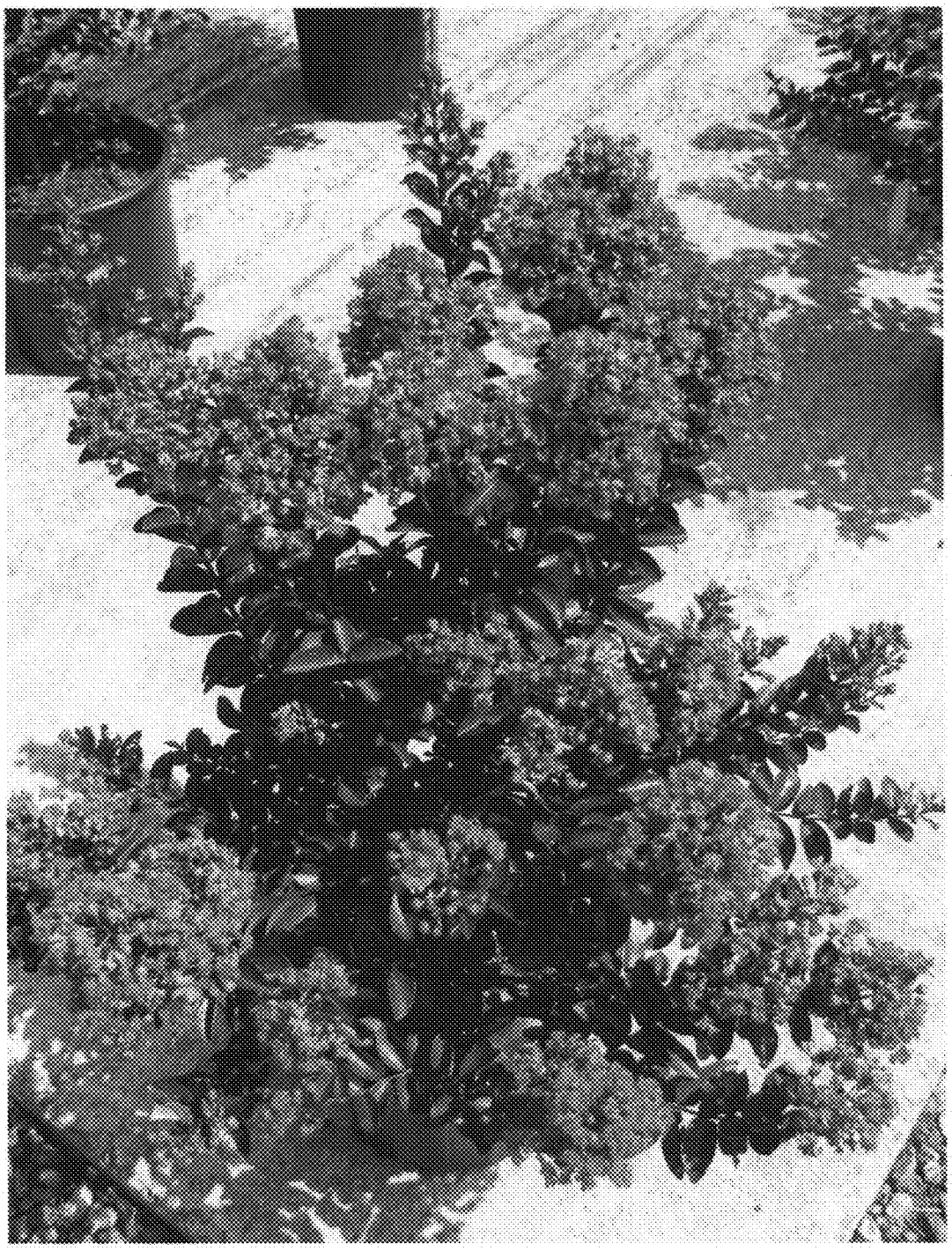
FIG. 2 illustrates the overall appearance of a plant of 'Purple Magic' in a container.
Figure 3:
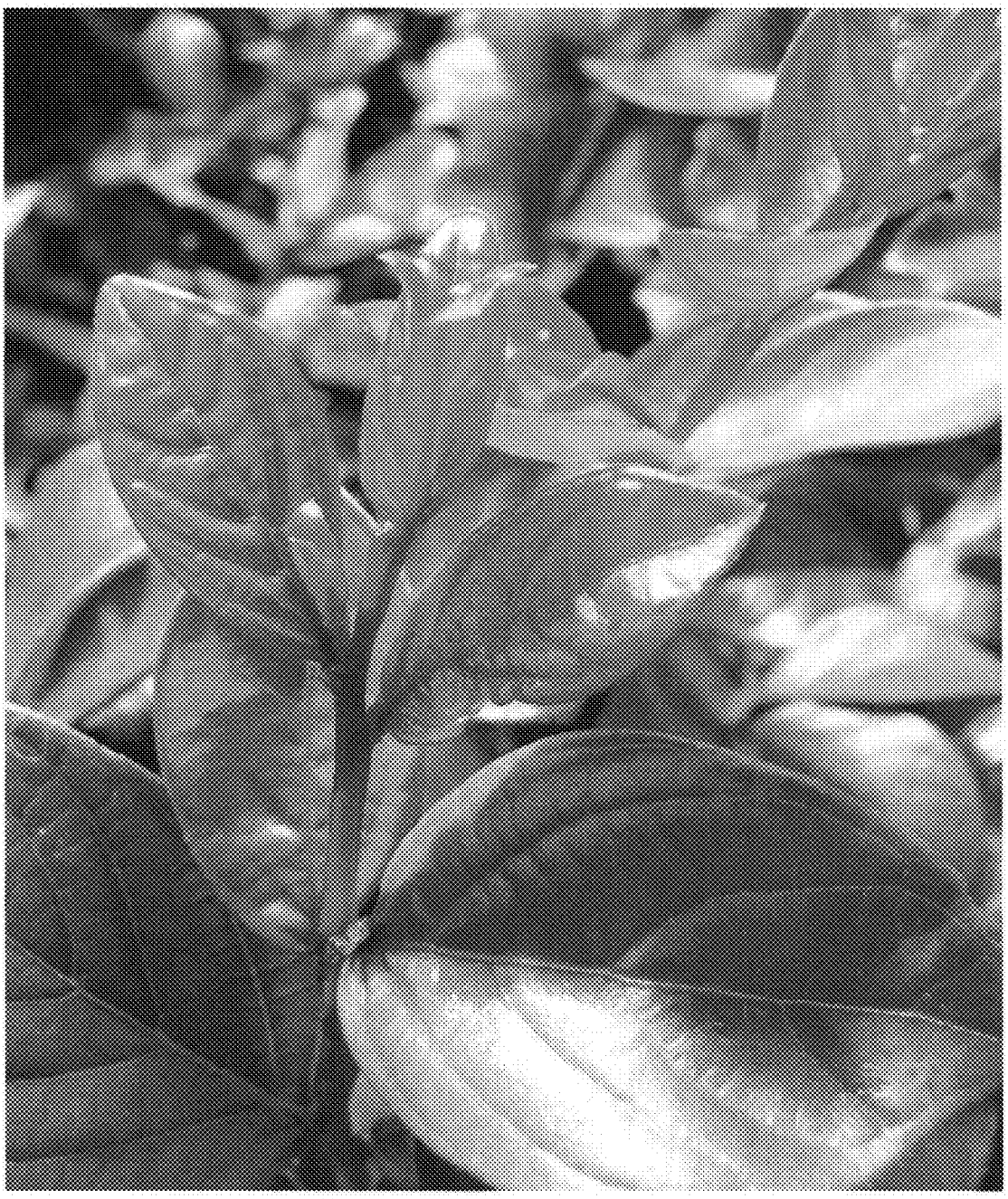
FIG. 3 illustrates a close-up view of the new growth of 'Purple Magic'.

In the following description, color references are made to The Royal Horticultural Society Colour Chart, 2001 Edition, except where general terms of ordinary dictionary significance are used. Plants used for the description were approximately two years old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'Purple Magic'.

Parentage:

*Female, or seed, parent.*—*Lagerstroemia* 16-02 (unpatented).

*Male, or pollen parent.*—Unknown (open-pollinated).

Propagation: Terminal cuttings.

Time to initiate roots, summer: About 21 days at 32° C.

Plant description:

*Flowering shrub.*—Compact, rounded to upright growth habit.

*Freely branching.*—Pruning enhances lateral branch development.

*Root description.*—Numerous, fine, fibrous and well-branched.

*Plant size.*—The original plant, now about four-years-old in the ground, is about 116 cm high from the soil level to the top of the inflorescences and about 90 cm wide. First year stems have a diameter of about 2.5 mm. Shape: squarish. Second year and older stems have a diameter of about 5 mm or more. Shape: round.

*Trunk diameter.*—3 cm at the soil line. Color: N199B.

*Internode length.*—About 1.9 cm.

*Strength.*—Flexible when young, easily broken once mature.

*First year stem color* (*young*).—183A. Color (woody): 200D.

*Second year and older stem color.*—N199B.

*Bark.*—Exfoliates in strips beginning on second or third year stems.

Vegetative buds: Sub-opposite to alternate in arrangement, imbricate, conical, with no pubescence.

*Color.*—183B.

*Size.*—About 2.5 mm in length and 1 mm in width.

Foliage description:

*Arrangement.*—Sub-opposite to alternate, simple.

*Length.*—About 4.7 cm.

*Width.*—About 2.5 cm.

*Shape.*—Elliptical.

*Apex.*—Acuminate.

*Base.*—Cuneate.

*Margin.*—Entire.

*Texture* (*upper and lower surfaces*).—Glabrous and glossy.

*Venation pattern.*—Pinnate.

*Venation color of emerging foliage* (*upper and lower surfaces*).—178B.

*Venation color of fully expanded foliage* (*upper and lower surfaces*).—178B at the base, changing to 35C at the apex.

*Color in developing foliage* (*upper and lower surfaces*) .—178B.

*Color in fully expanded foliage* (*upper surface*).—147A.

*Color in fully expanded foliage* (*lower surface*).—146B.

*Petiole length.*—About 2 mm.

*Petiole diameter.*—About 1 mm.

*Petiole color* (*upper and lower surfaces*).—177A.

*Pubescence.*—None.

Flower description: Flowers are produced from about June to September in Watkinsville, Ga. An inflorescence is showy for about two weeks, and individual flowers last about one day and are self-cleaning.

*Inflorescence type.*—Panicle.

*Inflorescence length.*—About 10 cm.

*Inflorescence width.*—About 8 cm.

*Peduncle.*—About 8 cm in length, about 2 mm in diameter, color is 183A, and no pubescence.

*Individual flowers.*—About 2 cm in height and 3.6 cm in diameter.

*Flower buds.*—Length: about 8 mm; Diameter: about 8 mm; Color: 178B.

*Pedicels.*—About 7 mm in length, 178B in color, and no pubescence. Pedicel diameter is about 1 mm.

*Sepals.*—6 per flower, about 9 mm in length, about 6 mm in width, acute apex, entire margin, and 176A in color on upper and lower surfaces.

*Calyx.*—About 9 mm in length, about 1.1 cm in diameter, 176A in color, and no pubescence.

Petals:

*Arrangement/appearance.*—Usually 6 or 7 per flower.

*Petal length.*—About 1.8 cm.

*Petal width.*—About 1.2 cm.

*Petal shape.*—Fan-shaped.

*Petal apex.*—Ruffled, rounded.

*Petal base.*—Sagittate.

*Petal margin.*—Ruffled.

*Petal texture* (*upper and lower surfaces*).—Glabrous.

*Petal color.*—Upper and lower surfaces are 77A.

Stamens:

*Quantity/arrangement.*—About 25 to 30 short stamens clustered in the center, about 8 mm long, filament color is 62B, and anther color is 13B. The short stamens are surrounded by 6 longer stamens, about 1.2 cm long, filament color is 63A, and anther color is N199C. The stamens are not pubescent.

*Pollen.*—Produced in moderate quantities and is 13B in color on the short stamens and 144C in color on the long stamens.

Pistils:

*Quantity.*—One superior pistil per flower.

*Pubescence.*—None.

*Pistil length.*—About 1.8 cm in length.

*Stigma shape.*—Round, about 1 mm in diameter.

*Stigma color.*—146A.

*Style color.*—183C and about 1.5 cm in length.

*Ovary color.*—5D and about 2 mm in diameter.

Fruit:

*Type/appearance.*—Six-valved, dehiscent, broad ellipsoidal capsule.

*Length.*—About 8 mm.

*Diameter.*—About 7 mm.

*Immature color.*—144A.

*Mature color.*—200C. Each capsule contains many seeds that are about 5 mm long, 3 mm wide, and 200C in color.

Disease/pest resistance: Plants of the claimed *Lagerstroemia* variety grown in field and container trials have exhibited resistance to powdery mildew and *Cercospora* leaf spot.

I claim:

1. A new and distinct *Lagerstroemia* plant named 'Purple Magic', as illustrated and described herein.

* * * * *